(12) United States Patent
Ladak et al.

(10) Patent No.: US 7,162,065 B2
(45) Date of Patent: *Jan. 9, 2007

(54) PROSTATE BOUNDARY SEGMENTATION FROM 2D AND 3D ULTRASOUND IMAGES

(75) Inventors: Hanif M. Ladak, Brantford (CA); Aaron Fenster, London (CA); Donal B. Downey, London (CA); David A. Steinman, London (CA)

(73) Assignee: John P. Robarts Research Instutute, London ( * ) Notice: Subject to any disclaimer, the term of this patent is extended or adjusted under 35 U.S.C. 154(b) by 40 days.

This patent is subject to a terminal disclaimer.

(21) Appl. No.: 10/856,854

(22) Filed: Jun. 1, 2004

(65) Prior Publication Data

US 2004/0218797 A1 Nov. 4, 2004

Related U.S. Application Data

(63) Continuation of application No. 09/373,954, filed on Aug. 13, 1999, now Pat. No. 6,778,690.

(51) Int. Cl.
G06K 9/00 (2006.01)

(52) U.S. Cl. .............. 382/131; 382/173; 382/177; 128/916

(58) Field of Classification Search ........ 382/128–134, 382/164, 171, 173, 177, 172, 179, 242, 256; 600/141, 407, 437, 516, 443, 445, 459; 601/2; 128/200.16, 915, 916
See application file for complete search history.

(56) References Cited

U.S. PATENT DOCUMENTS

| 5,454,371 A | | 10/1995 | Fenster et al. | |
|---|---|---|---|---|
| 5,457,754 A | * | 10/1995 | Han et al. ................ | 382/128 |
| 5,559,901 A | * | 9/1996 | Loregt ..................... | 382/256 |
| 5,562,095 A | | 10/1996 | Downey et al. | |
| 5,842,473 A | | 12/1998 | Fenster et al. | |
| 5,871,019 A | * | 2/1999 | Belohlavek .............. | 600/450 |
| 6,163,757 A | * | 12/2000 | Aizawa et al. ............ | 702/42 |
| 6,251,072 B1 | * | 6/2001 | Ladak et al. ............. | 600/443 |
| 6,272,233 B1 | * | 8/2001 | Takeo ..................... | 382/128 |

OTHER PUBLICATIONS

Elliot, et al., Accuracy of Prostate Volume Measurements In Vitro Using Three-Dimensional Ultrasound, *Academic Radiology*, vol. 3, No. 5, pp. 401-406 (May 1996).

Tong, et al., Intra- and Inter-observer Variability and Reliability of Prostate Volume Measurement Via Two-Dimensional and Three-Dimensional Ultrasound Imaging, *Ultrasound in Medicine and Biology*, vol. 24, No. 5, pp. 673-681, (1998).

Ku, Joy P., et al., Construction of Geometric Models From Arbitrarily Oriented 2D Ultrasound Images, *Bioengineering Conference*, Jun. 16-20, 1999, Big Sky Montana.

* cited by examiner

*Primary Examiner*—Jingge Wu
*Assistant Examiner*—Abolfazi Tabatabai
(74) *Attorney, Agent, or Firm*—Sim & McBurney

(57) ABSTRACT

A fast semi-automatic prostate contouring method is provided using model-based initialization and an efficient Discrete Dynamic Contour (DDC) for boundary refinement. The user initiates the process of the preferred embodiment by identifying four (4) points on the prostate boundary, thereby scaling and shaping a prostate model, and then the final prostate contour is refined with a DDC. The method of the present invention has particular application during the pre-implant planning phase of a brachytherapy procedure. However, this method also has uses in any phase of dose planning in the brachytherapy procedure or any other therapy approach.

10 Claims, 17 Drawing Sheets

1 (a)

1 (b)

1 (c)

1 (d)

4 (a)

4 (b)

4 (c)

9 (a)

9 (b)

11 (a)

11 (b)

11 (c)

11 (d)

13 (g)
 13 (h)
 13 (i)
 13 (j)
 13 (k)
 13(l)

PROSTATE BOUNDARY SEGMENTATION FROM 2D AND 3D ULTRASOUND IMAGES

This application is a continuation of U.S. application Ser. No. 09/373,954 filed on Aug. 13, 1999, now U.S. Pat. No. 6,778,690.

FIELD OF THE INVENTION

This invention relates in general to medical imaging systems, and more specifically to a method of prostate boundary segmentation from 2D and 3D ultrasound images.

BACKGROUND OF THE INVENTION

Prostate cancer is the most commonly diagnosed malignancy in men over the age of 50, and is found at autopsy in 30% of men at the age of 50, 40% at age 60, and almost 90% at age 90. Worldwide, it is the second leading cause of death due to cancer in men, accounting for between 2.1% and 15.2% of all cancer deaths. In Canada, about 20,000 new prostate cancer cases will be diagnosed and about 4,000 men will die from this disease every year.

Symptoms due to carcinoma of the prostate are generally absent until extensive local growth or metastases develop, accounting for the fact that only 65% of patients are diagnosed with locally confined disease. Once the tumour has extended beyond the prostate, the risk of metastasis increases dramatically. Tumours smaller than 1 to 1.5 cm$^3$ rarely broach the prostatic capsule. When diagnosed at this early stage, the disease is curable, and even at later stages treatment can be effective. Nevertheless, treatment options vary depending on the extent of the cancer, and prognosis worsens when diagnosis occurs at an advanced stage.

The challenges facing physicians managing patients with possible prostate cancer are to: (a) diagnose clinically relevant cancers at a stage when they are curable, (b) stage and grade the disease accurately, (c) apply the appropriate therapy accurately to optimize destruction of cancer cells while preserving adjacent normal tissues, (d) follow patients to assess side effects and the effectiveness of the therapy.

U.S. Pat. Nos. 5,562,095, 5,454,371 and 5,842,473 focused on challenges (a) and (b). These patents describe a 3D ultrasound imaging technique for the diagnosis of prostate cancer. Extension of these concepts for prostate cryosurgery are described in commonly assigned U.S. Patent application Ser. No. 60/321,049, the contents of which are incorporated herein by reference. An important aspect in the establishment of the appropriate prostate therapy is the accurate segmentation (i.e., extraction) of the prostate boundary and other anatomical structures (rectal wall, urethra, bladder). Assignment of the appropriate therapy or dose to the prostate requires that the prostate volume be accurately measured.

In situations where the image contrast is great (e.g., in fluid filled regions in ultrasound images), the segmentation task is relatively easy and many approaches can be used. However, ultrasound images of the prostate are very difficult to segment because the contrast is low, and the image suffers from speckle, shadowing and other artifacts. In performing ultrasound image segmentation, traditional local image processing operators like edge detectors are inadequate in and of themselves for finding the boundary, due to speckle, shadowing and other image artifacts.

The variability in prostate volume measurements using a conventional 2D technique is high, because current ultrasound volume measurement techniques assume an idealized elliptical shape and use only simple measures of the width in two views (see Tong S, Cardinal H N, McLoughlin R F, Downey D B, Fenster A, "Intra- and inter-observer variability and reliability of prostate volume measurement via 2D and 3D ultrasound imaging", Ultrasound in Med & Biol 1998; 24:673–681, and Elliot T L, Downey D B, Tong S, Mclean C A, Fenster A, "Accuracy of prostate volume measurements in vitro using three-dimensional ultrasound", Acad Radiol 1996; 3:401–406).

Manual contouring of sequential cross-sectional 2D CT or TRUS (transrectal ultrasound) prostate images has reduced this variability, but this approach is time-consuming and arduous, making it impractical during an intra-operative procedure.

Region-based neural net approaches require extensive teaching sets, are slow, and make addition of user specified boundary information difficult. Contour-based methods, such as "snakes" implementation of active contours are slow, complex, and sensitive to the initial choice of contour.

SUMMARY OF THE INVENTION

According to the present invention, a fast semi-automatic prostate contouring method is provided using model-based initialization and an efficient Discrete Dynamic Contour (DDC) for boundary refinement. The user initiates the process of the preferred embodiment by identifying four (4) points on the prostate boundary, thereby scaling and shaping a prostate model, and then the final prostate contour is refined with a DDC.

The method of the present invention can encompass a 2D segmentation technique or alternatively extend to the segmentation of objects in 3D.

The method of the present invention has particular application during the pre-implant planning phase of a brachytherapy procedure. However, this method also has uses in any phase of dose planning in the brachytherapy procedure or any other therapy approach.

BRIEF DESCRIPTION OF THE DRAWINGS

Various embodiments of the present invention are described below with reference to the drawings in which:

FIG. 1(a)–1(d) shows a prior art segmentation technique using DDC, wherein FIG. 1(a) shows an initial DDC drawn by the user, FIG. 1(b) shows the early stage of deformation, FIG. 1(c) shows the later stage of deformation, and FIG. 1(d) shows the final deformed DDC.

FIGS. 4(a)–4(c) shows image energy and force field for a vertical edge of an ultrasound image, wherein FIG. 4(a) shows the edge modeled as a step edge (i.e., an edge wherein there is a drastic transition in gray levels, FIG. 4(b) shows the energy field associated with the edge, and FIG. 4(c) shows the image force field.

FIGS. 9(a) and 9(b) shows a first example of operation of the prostate segmentation algorithm of the present invention wherein FIG. 9(a) shows an initial outline with four user-selected points, and FIG. 9(b) shows the final segmented outline obtained after deforming the DDC.

FIGS. 10(a)–10(b) shows the steps of segmentation and editing in a second example of operation of the present invention in which portions of the DDC do not follow the prostate boundary very well, wherein FIG. 10(a) shows an initial outline with four user-selected points, FIG. 10(b) shows the DDC after a first deformation, FIG. 10(c) shows three vertices (shown as squares) which are edited and clamped, followed by further deformation of the DDC, and FIG. 10(d) shows the outline after second deformation.

FIGS. 11(a)–11(d) shows the segmentation of a "difficult" case according to the present invention, wherein FIG. 11(a) shows the initial outline with four user-selected points, FIG. 11(b) shows the DDC after first deformation, FIG. 11(c) shows five vertices (shown as squares) edited and clamped, and followed by a further deformation of the DDC, and FIG. 11(d) shows the outline after second deformation.

FIGS. 13(a)–13(ii) shows a sequence of 2D images of the prostate segmented using the semi-automatic segmentation procedure extended to 3D. The images are parallel to each other separated by 1 mm. Image no. 15 was used to initiate the process by the semi-automatic 2D segmentation technique. Subsequent to the segmentation of that 2D image, the final boundary was used to initiate the segmentation of the next image.

This process was repeated until the complete prostate was segmented.

DETAILED DESCRIPTION OF THE PRIOR ART
AND OF THE PREFERRED EMBODIMENT

As discussed above, DDC is a poly-line (i.e., a sequence of points connected by straight-line segments) used to deform a contour to fit features in an image. When using the DDC to segment an object from an image as originally described by Lobregt and Viergever in "A discrete dynamic contour model", IEEE Trans. Med. Imag. 1995; 14:12–24, the user must first draw an approximate outline of the object. An example outline is shown in FIG. 1(a) for a typical 2D US (ultrasound) image of the prostate. The DDC is initialized to this outline and is automatically deformed to fit features of interest, which in this case consist of edges that define the boundary of the prostate. FIGS. 1(b) and 1(c) show two stages in the deformation of the DDC. Note that points are automatically added to or deleted from the DDC as it deforms to allow it to better conform to the boundary. FIG. 1(d) shows the final deformed DDC. In this example, the final shape conforms well to the prostate boundary except in some areas where artifacts and noise in the image cause parts of the DDC to deform towards them and away from the prostate boundary.

Figure 2:
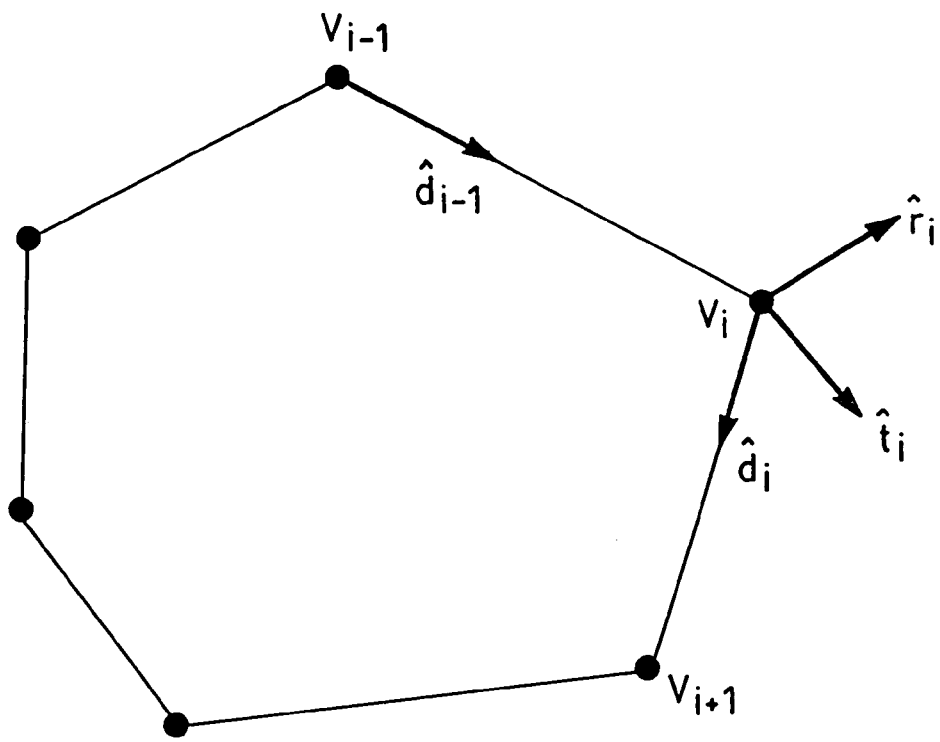
FIG. 2 shows an example of configuration of the prior art DDC.

The configuration of the DDC is shown in FIG. 2. As illustrated, the unit edge vector $\hat{d}_i$ points from vertex i to vertex i+1. A local tangential unit vector, $\hat{t}_i$, is $$\hat{t}_i = \frac{\hat{d}_i + \hat{d}_{i-1}}{\|\hat{d}_i + \hat{d}_{i-1}\|} \quad (1)$$

defined at vertex i from the two edge vectors associated with the vertex:

where $\|\cdot\|$ denotes magnitude of a vector. A local radial unit vector $\hat{r}_i$ can be computed from $\hat{t}_i$ by rotating it by B/2 radians:

$\hat{r}_i$ and $\hat{t}_i$ define a local coordinate system attached to vertex i.

$$\hat{r}_i = \begin{bmatrix} 0 & 1 \\ -1 & 0 \end{bmatrix} \hat{t}_i. \quad (2)$$

Figure 3:
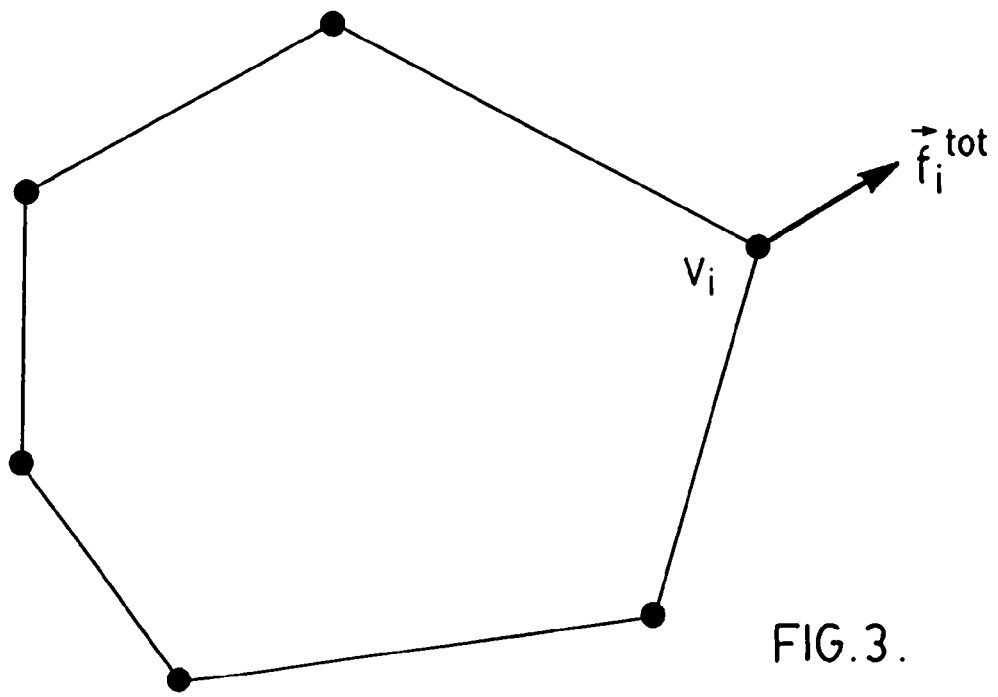
FIG. 3 shows forces as vector quantities having both direction and magnitude, for the configuration of FIG. 2.
Figure 4:
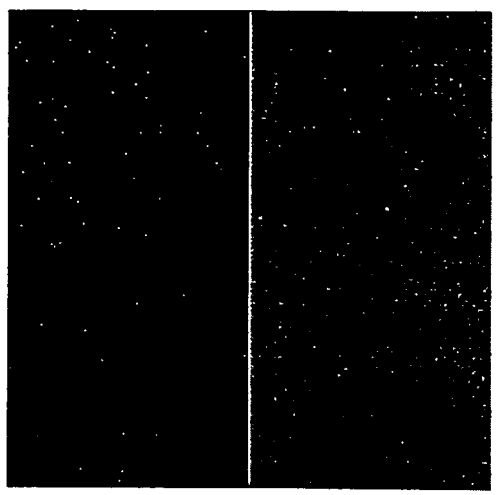
Figure 4:
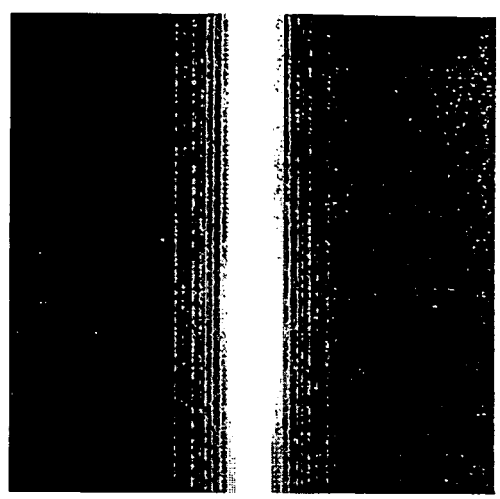
Figure 4:
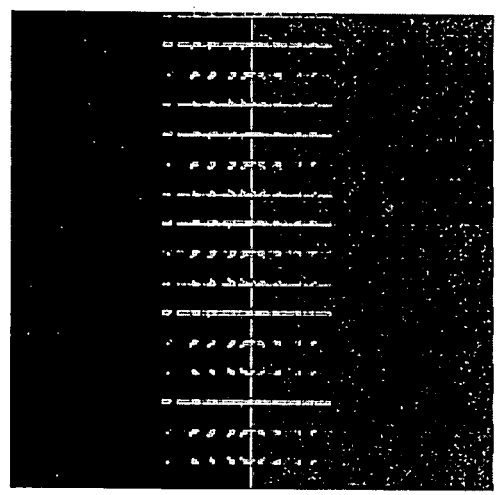

The operation of the DDC is based on simple dynamics. A weighted combination of internal ($-\vec{f}_i^{int}$), image ($\vec{f}_i^{img}$) and damping ($\vec{f}_i^{d}$) forces is applied to each vertex i of the DDC, resulting in a total force $\vec{f}_i^{tot}$:

$$\vec{f}_i^{tot} = w_i^{int} \vec{f}_i^{int} + w_i^{img} \vec{f}_i^{img} + \vec{f}_i^{d} \quad (3)$$

where $w_i^{img}$ and $w_i^{int}$ are relative weights for the image and internal forces, respectively. It should be noted that these forces are vector quantities, having both magnitude and direction as shown in FIG. 3. For the prostate, image forces act to drive vertices towards the edges. These forces can be defined at each pixel of the $$E(x, y) = \left\| \vec{\nabla}(G_\sigma * I(x^p, y^p)) \right\| \quad (4a)$$

$$\vec{f}_i^{img}(x, y) = \frac{2\vec{\nabla} E(x^p, y^p)}{\max \left\| \vec{\nabla} E(x^p, y^p) \right\|} \quad (4b)$$

image as:

where E represents the "energy" associated with a pixel having coordinates ($x^p$, $y^p$), $G_{101}$ is a Gaussian smoothing kernel with a characteristic width of Φ and I is the image. The * operator represents convolution, and $\vec{\nabla}$ is the gradient operator. The energy has a local maximum at an edge, and the force computed from the energy serves to localize this edge. The factor of two in Equation (4b) gives the magnitude of the image force a range of zero to two, which is the same as that for the internal force defined below. A sample energy field and its associated force field for a simulated image of an edge are shown in FIGS. 4(a) to 4(c). It should be noted that image forces have effect over a limited spatial extent around an edge as shown by the concentration of energy around the edge in FIG. 4(b). The extent of this "capture range" is determined by σ in Equation 4(a), and becomes larger as σ becomes larger. Although a large capture range is desirable to compensate for deficiencies in the initial outlining of the DDC by the user (e.g., some vertices on the initial DDC may be outside of the capture range), a large value of σ can result in poor localization of the desired edge. A large σ also offers the advantage of increased noise suppression. According to a successful implementation of the present invention, for prostate images, a value of σ=5 pixels was selected as a compromise.

To evaluate the image force acting on vertex i of the DDC, the force field represented by Equation (4b) is sampled at vertex coordinates $(x_p, y_i)$ using bilinear interpolation. Furthermore, only the radial component of the field is applied at the vertex since the tangential component can potentially cause vertices to bunch up as the DDC deforms, so the resultant image force at vertex i is:

$$\vec{f}_i^{img} = \left( \vec{f}^{img}(x_i, y_i) \cdot \hat{r}_i \right) \hat{r}_i \quad (5)$$

where · denotes a vector dot product.

Figure 5A:
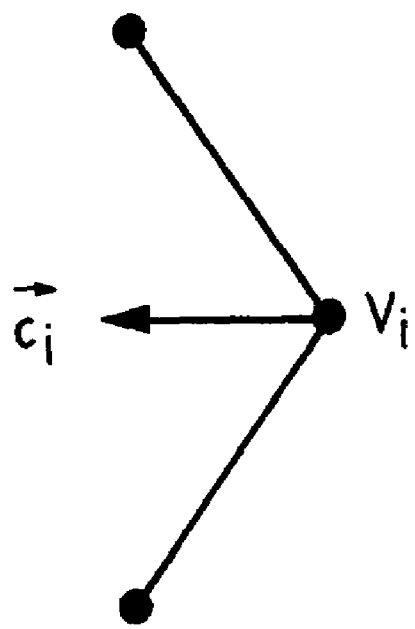
FIGS. 5(a) and 5(b) are a representation of a curvature vector, {character pullout} as a measure of angle between edges for 5(a) a large curvature, and 5(b) a small curvature.
Figure 5B:
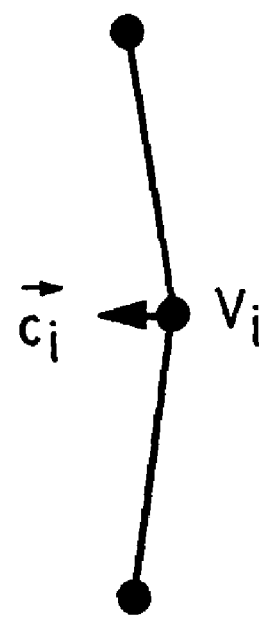

The internal force acts to minimize local curvature at each vertex, keeping the DDC smooth in the presence of image noise. It is defined as:

$$\vec{f}_i^{int} = \left( \vec{c}_i \cdot \hat{r}_i - \frac{1}{2}(\vec{c}_{i-1} \cdot \hat{r}_{i-1} + \vec{c}_{i+1} \cdot \hat{r}_{i+1}) \right) \hat{r}_i \quad (6)$$

$$\vec{c}_i = \hat{d}_i - \hat{d}_{i-1} \quad (7)$$

where is the curvature vector at vertex i. The curvature vector is a measure of the angle between two edges as shown in FIGS. 5(a) and 5(b) Although simply taking $\vec{f}_i^{int}$ to be proportional to $\vec{c}_i$ could achieve the goal of minimizing local curvature, the definition in Equation (6) has the advantage of preventing the DDC from collapsing to a point in the absence of image forces.

The damping force at vertex i is taken to be proportional to the velocity ($\vec{v}_i$) at that vertex:

$$\vec{f}_i^d = w_i^d \vec{v}_i \quad (8)$$

where $w_i^d$ is a negative weighting factor. The damping force keeps the DDC stable (i.e., prevents oscillations) during deformation.

Figure 1:
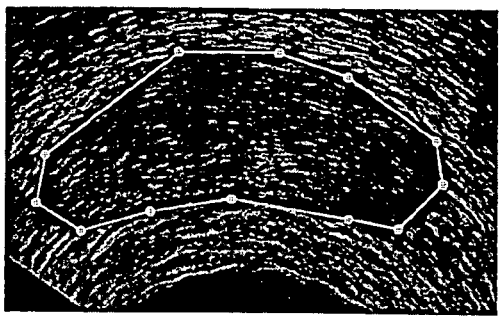
Figure 1:
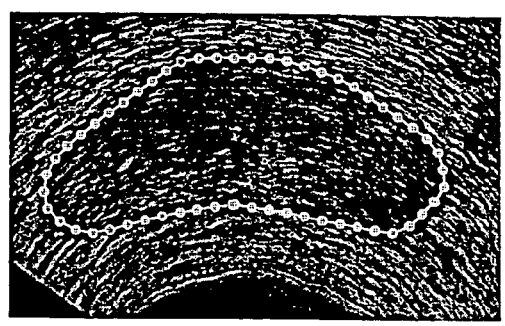
Figure 1:
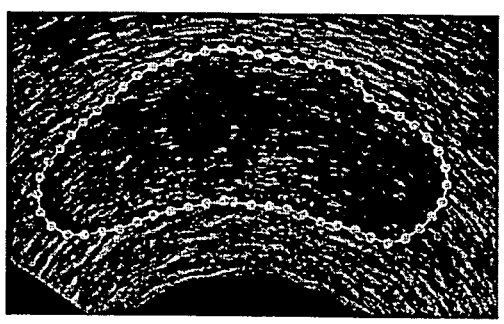
Figure 1:
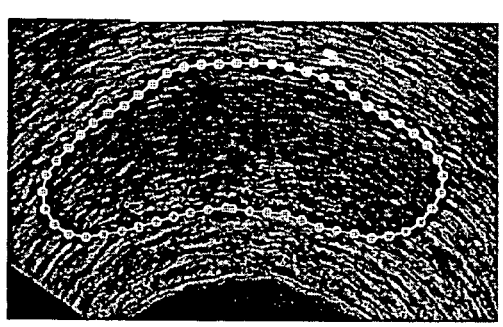

For simplicity, uniform weights for the image, internal and damping forces were selected for the result shown in FIG. 1 and for all subsequent segmentations. The weights were taken to be $w_i^{img}=1.0$, $w_i^{int}=0.3$ and $w_i^d=-0.5$ for each vertex. Although these values were selected experimentally, the larger weighting for the image force favors deformation of the contour towards edges rather than smoothing due to internal forces. Had the images been much noisier, a larger weight would have been given to the internal forces. The selection of a weight for the damping force appears to be less critical, and a small negative value was found to provide good stability.

Figure 6:
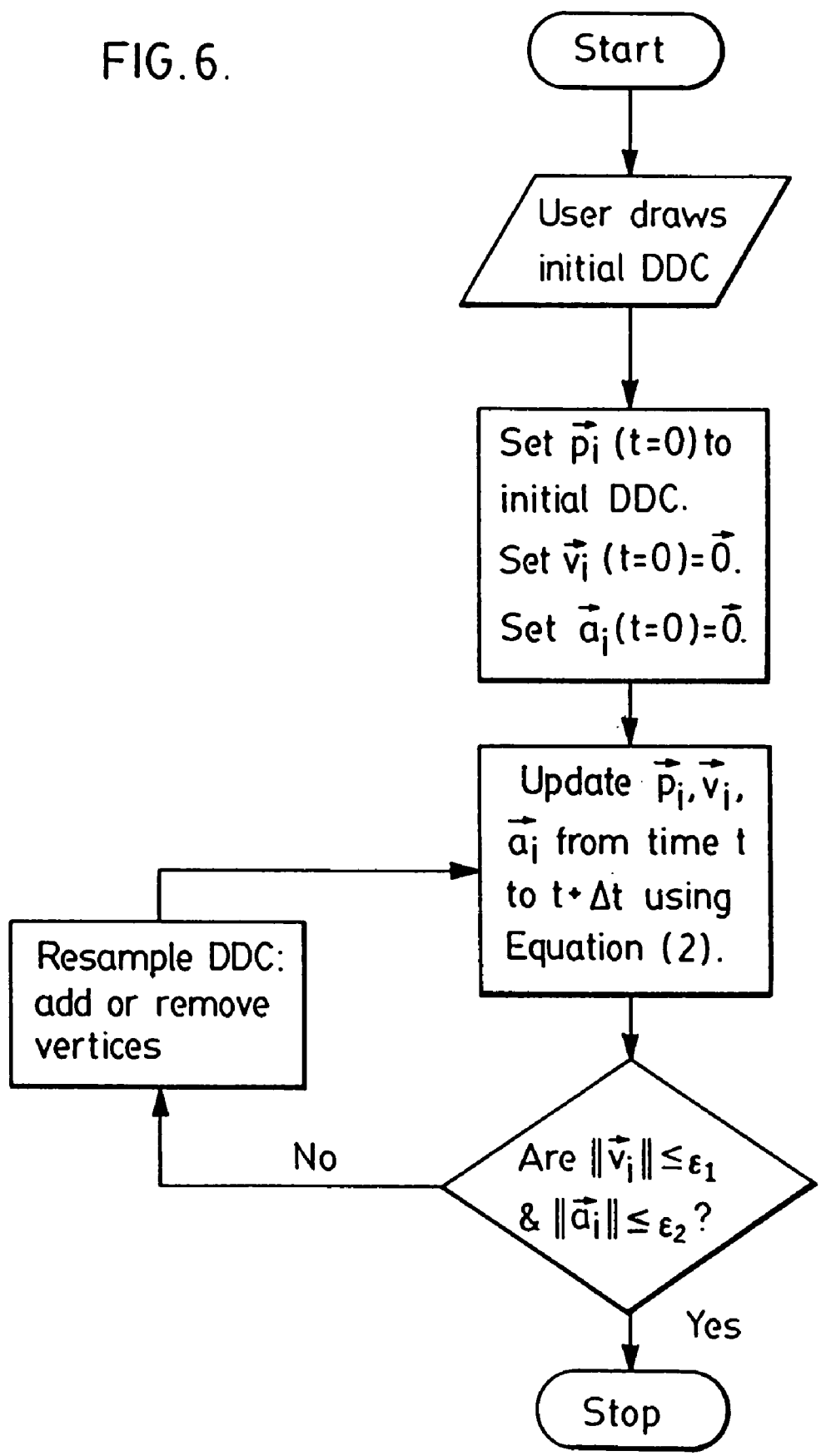
FIG. 6 Flow chart showing implementation of the DDC deformation process utilized in the method of the present invention.

Deformation of the DDC is governed by the above forces and is implemented as a simple numerical integration, depicted in FIG. 6. The position of vertex i on the DDC at time t+Δt is calculated from its position at time t using the following finite-difference equations:

$$\vec{p}_i(t + \Delta t) = \vec{p}_i(t) + \vec{v}_i(t)\Delta t \quad (9a)$$

$$\vec{v}_i(t + \Delta t) = \vec{v}_i(t) + \vec{a}_i(t)\Delta t \quad (9b)$$

$$\vec{a}_i(t + \Delta t) = \frac{1}{m_i}\vec{f}_i(t + \Delta t). \quad (9c)$$

where $\vec{p}_i$ is the position of the vertex, $\vec{a}_i$ is its acceleration, $m_i$ is its mass and Δt is the time step for numerical integration. For simplicity, the mass of each vertex is taken to be unity. The initial position of each vertex (i.e., the position at t=0) is specified by the user-drawn contour, and the initial velocity and acceleration are set to zero. The position, velocity and acceleration of each vertex are then iteratively updated using the above equations. After each iteration, the DDC is "resampled" to add or remove vertices from it as described in greater detail below. Iterations continue until all vertices come to a rest, which occurs when the velocity and acceleration of each vertex become approximately zero (i.e., when $\|\vec{v}_i\| \leq \epsilon_1$ and $\|\vec{a}_i\| \leq \epsilon_2$ where $\epsilon_1$ and $\epsilon_2$ are two small positive constants close to zero). A time step of unity is used for the integration.

As discussed above, because 2D US images of the prostate suffer from speckle, shadowing and refraction, the boundary of the prostate is, at times, difficult to define. In addition, the contrast between the prostate and surrounding structures is low and dependent on the system's transducer and ultrasound frequency. These effects combine to make the choice of initial boundary crucial in allowing the DDC to converge to the correct boundary. Vertices on the DDC must be initialized close enough to the desired boundary to be attracted to it and not to nearby extraneous edges. Accurate initialization can require substantial user effort since the user may be required to enter many points as shown in FIG. 1(a). To overcome this problem, according to the present invention prostate-specific shape information is incorporated into the initialization phase. With this approach, it is possible to obtain a good estimate of the prostate boundary with very little user input. Even with good initialization, it is possible for the DDC to converge on strong non-prostate edges that are nearby. The incorporation of gradient direction information into the image force field can reduce the attraction of such features.

Figure 7:
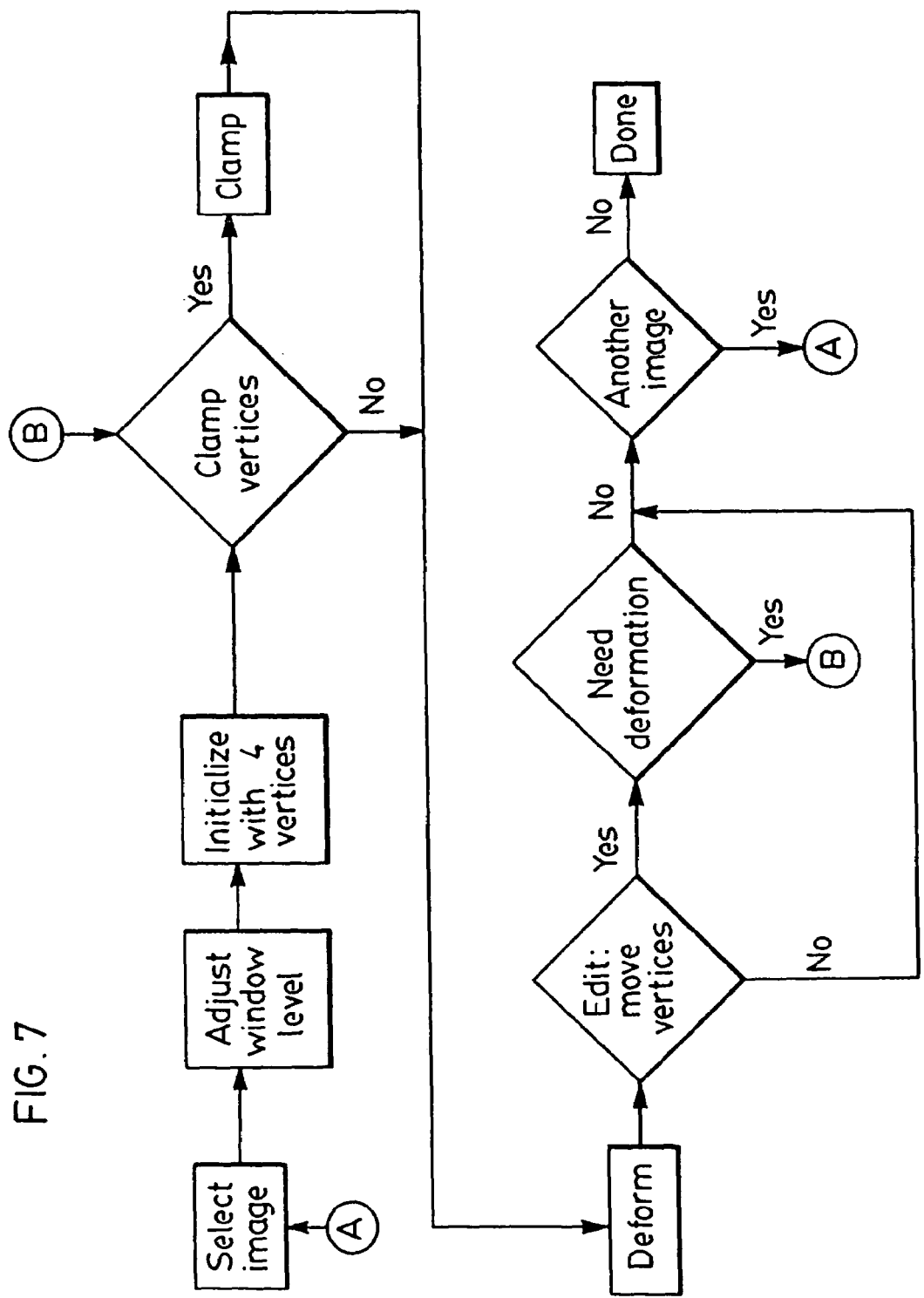
FIG. 7 is a flowchart for the 2D segmentation algorithm according to the present invention.

The algorithm of the present invention consists of three main phases: initialization, deformation and editing. Each process is described in detail below. The interaction of these processes is shown in FIG. 7. After having selected an image and adjusting the window and level, the user must initialize the DDC by selecting four points on the boundary. The user may select to clamp the four points, i.e., make them immobile. The initial DDC is then deformed. If the DDC does accurately represent the prostate boundary after being deformed, it may be edited by allowing the user to interactively move vertices and clamp them. The edited DDC may be further deformed if needed.

Figure 8:
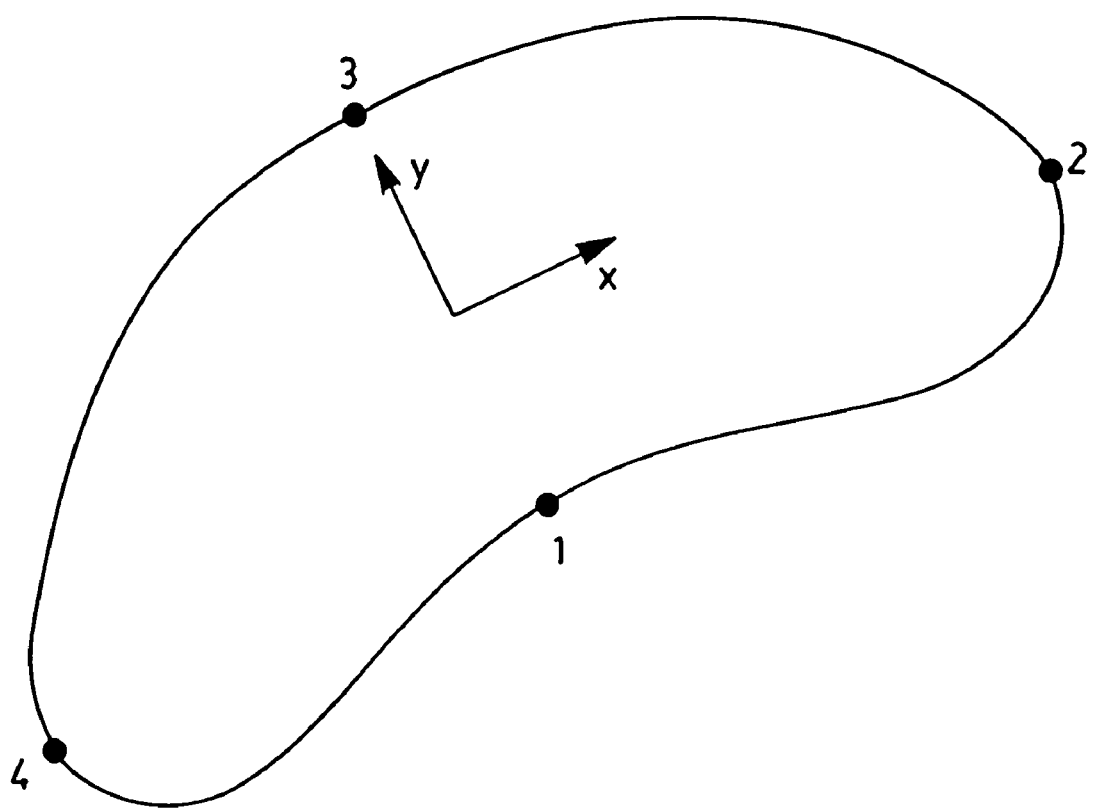
FIG. 8 shows the location of four user-selected points, labeled (1) to (4), on a prostate boundary, according to the method of the present invention.

As mentioned above, the DDC initialization routine of the present invention requires the user to select only four points, labeled from (1) to (4) in FIG. 8. Points (1) and (3) lie on the approximate axis of symmetry. A local x-y coordinate system may be defined by orienting the y axis from point (1) to point (3). The x axis is then taken to be perpendicular to they axis, and is oriented such that the cross product of the unit vector along the x axis and they axis (i.e., $\hat{x} \times \hat{y}$) points out of the screen. The origin of the coordinate system is taken to be the average of points (1) and (3).

If the initial shape of the DDC is represented in parametric form as:

$$\vec{p}(s) = \begin{Bmatrix} x(s) \\ y(s) \end{Bmatrix} \tag{10}$$

where s is a parameter that varies along the curve, then points (2) and (4) are selected on the "lobes" of the prostate where the local tangent to the curve at these points is parallel to they axis, i.e., points where $$x'(s)=0. \tag{11}$$

The ' operator denotes differentiation with respect to s.

The four points decompose the prostate boundary into four distinct segments: segment 1-2 which starts from point 1 and ends at point 2 as well as segments 2-3, 3-4 and 4-1. The initial shape of the prostate is estimated by Hermitian interpolation of the endpoints to automatically obtain additional points within each segment. Cubic interpolation functions were found to provide a good approximation to a large range of prostate shapes, and have the following form:

$$x(s)=a_3 s^3+a_2 s^2+a_1 s+a_0 \tag{12a}$$

$$y(s)=b_3 i\, s^3+b_2 s^2+b_1 s+b_0 \tag{12b}$$

where s is a parameter which varies from 0 at the starting point of the segment to 1 at the ending point and $a_i$ and $b_i$ (i=0, 1, 2, 3) are coefficients.

To interpolate additional points within a segment, it is first necessary to calculate the coefficients of Equation (12). Two pieces of data are required at each endpoint: the value of the variable (either x or y) and the rate of change of that variable with respect to s (x' or y'). Table 1 summarizes the information required for each segment. In the table, each segment is assumed to start at s=0 and end at s=1. Several points should be noted.

First, the tangents at points (1) and (3) are approximately parallel to the x axis, i.e., at these points we have $$y'(s)=0. \tag{13}$$

Here, the rate of change of x with respect to s is estimated from the user-selected points as listed in Table 1, which shows the data required to calculate coefficients for interpolation functions for each segment (1-2, 2-3, 3-4 and 4-1), where $(x_1,y_1)$, $(x_2,y_2$ $(x_3, y_3)$ and $(x_4, y_4)$ refer to the coordinates of the four user-selected points shown in FIG. 3.

Second, at points (2) and (4) where Equation (11) holds, the rate of change of y with respect to s must also be estimated as listed in the table. With these data, the coefficients can then be calculated using the formulae:

$$a_0=x(0)\ a_2=3(x(1)-x(0))-x'(1)-2x'(0)\, a_1=x'(0)\ a_3=2(x(0)-x(1))+x'(0)+x'(1) \tag{14a}$$

and $$b_0=y(0)\ b_2=3(y(1)-y(0))-y'(1)-2y'(0)\, b_1=y'(0)\ b_3=2(y(0)-y(1))+y'(0)+y'(1) \tag{14b}$$

Once the coefficients are calculated, points are uniformly interpolated within each segment at every Δs=0.1 units. FIG. 9(a) shows the initial DDC estimated for the prostate image shown in FIG. 1.

TABLE 1

|  | x(s) | | | | y(s) | | | |
| --- | --- | --- | --- | --- | --- | --- | --- | --- |
|  | x(0) | x(1) | x'(0) | x'(1) | y(0) | y(1) | y'(0) | y'(1) |
| 1–2 | $x_1$ | $x_2$ | $x_2 - x_4$ | 0 | $y_1$ | $y_2$ | 0 | $y_3 - y_1$ |
| 2–3 | $x_2$ | $x_3$ | 0 | $x_4 - x_2$ | $y_2$ | $y_3$ | $y_3 - y_1$ | 0 |
| 3–4 | $x_3$ | $x_4$ | $x_4 - x_2$ | 0 | $y_3$ | $y_4$ | 0 | $y_1 - y_3$ |
| 4–1 | $x_4$ | $x_1$ | 0 | $x_2 - x_4$ | $y_4$ | $y_1$ | $y_1 - y_3$ | 0 |

After initialization, the DDC is deformed as described in detail above. The four user-selected points chosen during the initialization phase can be clamped prior to deformation to prevent them from moving or they can be unclamped allowing them to move with the rest of the DDC.

Although the initialization routine of the present invention is able to represent a wide range of prostate shapes, the initial shape may fall near strong edges representing other tissues or artifacts. These may pull the DDC towards them and away from the desired (prostate) boundary if the image forces defined by Equations (4) and (5) are used. The attraction of such boundaries can be reduced by using directional information, as descibed in Worring M, Smeulders A W M, Staib L H, Duncan, J S, "Parameterized feasible boundaries in gradient vector fields", Computer Vision Image Understanding 1996; 63:135–144. For US images of the prostate, this information represents the fact that the interior of the prostate appears darker than the exterior. Such information can be applied at vertex i of the DDC by modifying Equation (5):

$$\vec{f}_i^{img} = \begin{cases} \left(\vec{f}^{img}(x_i, y_i) \cdot \hat{r}_i\right) \hat{r}_i, & \text{if } \hat{r}_i \cdot \vec{\nabla}(G_\sigma * I(x_i, y_i)) \geq 0 \\ 0, & \text{otherwise} \end{cases} \tag{15}$$

It is important to note that $\hat{r}(x,y)$ is an outward-pointing unit radial vector as defined by Equation (2). According to Equation (15), if the gray levels in the vicinity of vertex i vary from dark to light in the direction of the outer radial vector, a force is applied to the vertex; otherwise, no force is applied. FIG. 9(b) shows the DDC after deformation.

During deformation, the distance between adjacent vertices on the DDC can become larger, resulting in poor representation of the prostate boundary. After each iteration represented by Equation (9), the DDC is resampled so the distance between adjacent vertices is maintained at a uniform value of 20 pixels, which has been found to provide a good representation of the prostate boundary. When no vertices are clamped, resampling can be done very easily. First, the x and y coordinates of each vertex are represented in parametric form as in Equation (10). However, the parametric variable s is chosen to be the length of the curve from the first vertex to the vertex in question. The curve is then resampled along its entire length at equally-spaced values of length by linear interpolation of the existing vertices. This results in a new set of vertices which are used to represent the curve, with the old ones being discarded; This approach presents a problem when some vertices are clamped since the clamped vertices may be eliminated after interpolation. To avoid this, clamped vertices are simply inserted back into the DDC after interpolation.

In extreme cases, the initialization routine may not place all of the vertices on the DDC close to the actual prostate boundary. FIG. 10(a) shows an example where some portions of an initial DDC (indicated by the arrows) are distant from the prostate boundary. As shown in FIG. 10(b), this portion of the DDC does not converge on the desired boundary since image forces have a limited capture range. It is possible to correct the segmented boundary by editing the DDC and re-deforming it. The user can drag a vertex on the DDC towards the desired boundary. The vertex may then be "clamped" so it does not move when the DDC is re-deformed. FIG. 10(c) shows a case where three vertices (as indicated by the squares) have been dragged closer to the prostate boundary and clamped. When a vertex is moved and clamped, adjacent vertices generally deform towards the clamped vertex under the influence of internal forces to minimize local curvature. If these vertices move to within the capture range of the prostate boundary, image forces carry the vertices the rest of the way to the boundary. The DDC after deforming it again is shown in FIG. 10(d).

Figure 9:
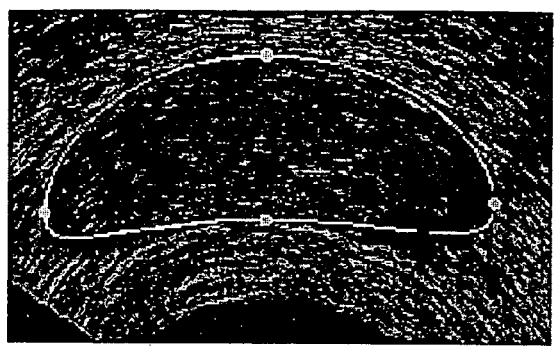
Figure 9:
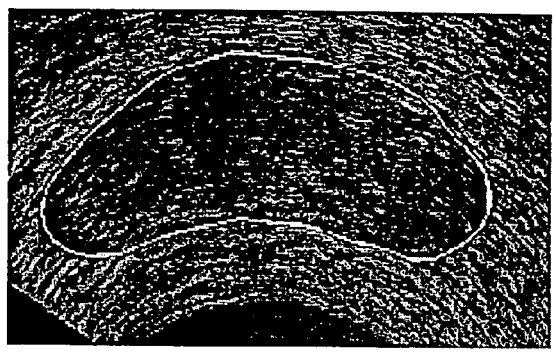
Figure 10:
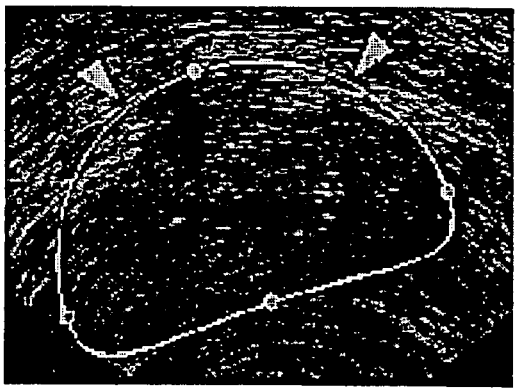
Figure 10:
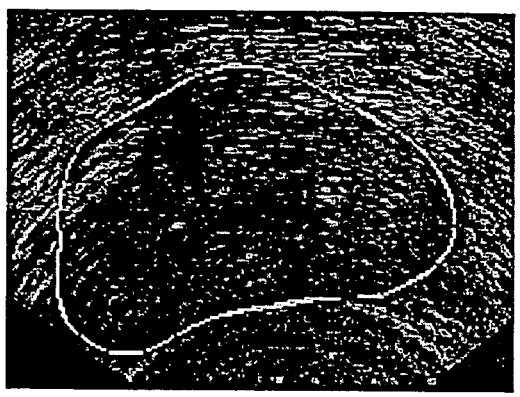
Figure 10:
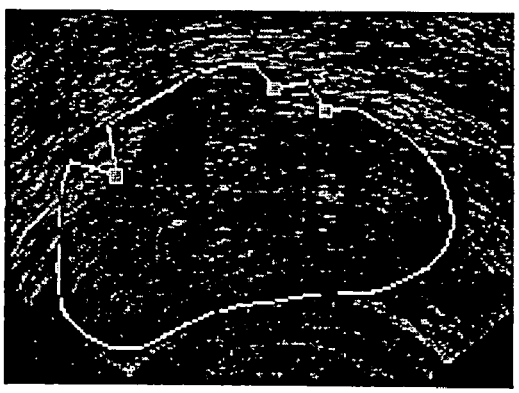
Figure 10:
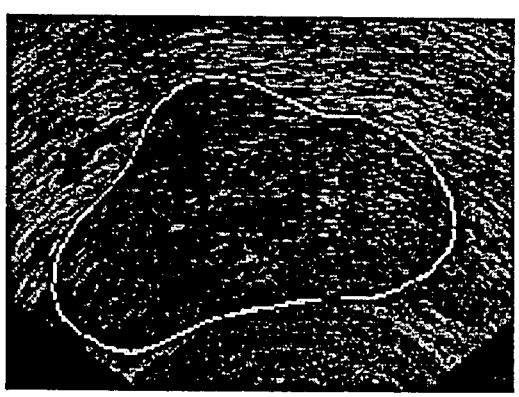
Figure 11:
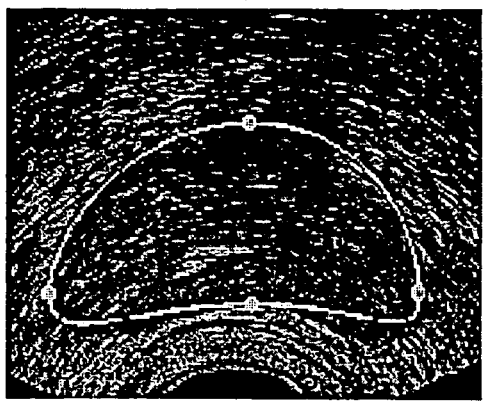
Figure 11:
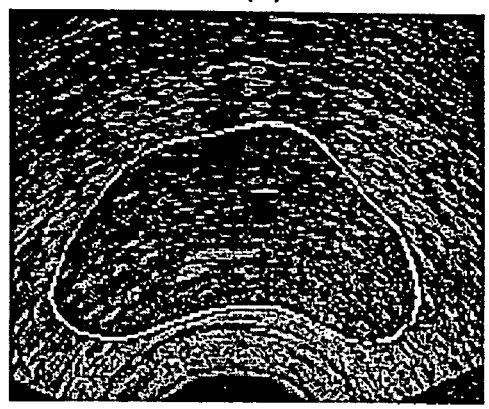
Figure 11:
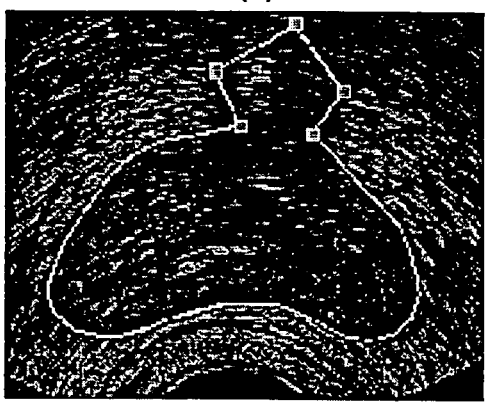
Figure 11:
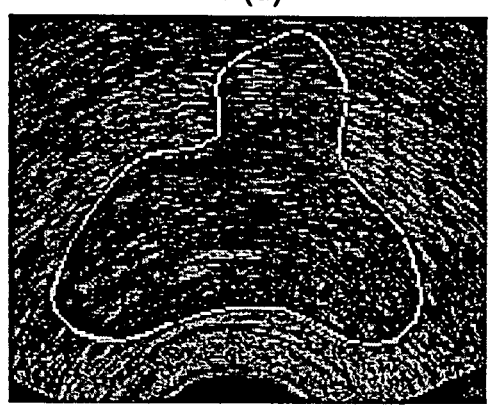

The examples in FIGS. 9 and 10 represent cases that are of "little" or "medium" difficulty to segment. A more challenging example is shown in FIG. 11 where the prostate has a bulge at the top. This shape is difficult to initialize with cubic interpolation shape functions. One contouring strategy is to initialize the DDC by ignoring the bulge as shown in FIG. 11(a). The DDC does not deform into the bulge as shown in FIG. 11(b). Vertices along the top can be dragged and clamped into position as shown in FIG. 11(c). The final segmented outline is shown in FIG. 11(d).

Other embodiments and variations are possible. For example, although the preferred embodiment set forth herein addresses the problem of prostate segmentation, the principles of the invention may be applied to boundary segmentation of any solid object, including other organs within the human or animal anatomy, provided suitable modifications are made to the interpolations functions used to initialize the boundary prior to deformation.

Also, whereas the method according to the preferred embodiment is set forth as a 2D segmentation technique, it can be extended to segmentation of objects, such as the prostate, in 3D. Because the surface of the organ is continuous, a 2D image slice which is separated by only a small spacing from adjacent parallel slices is characterized by a similar boundary to the boundaries of the adjacent slices. Thus, by slicing an object (i.e. organ) in parallel slices with a sufficiently small spacing, the boundary of the object in adjacent 2D slices will be similar. Accordingly, the segmented boundary in one slice may be used as an initial boundary for the segmentation process in the adjacent slices. If the object boundaries are sufficiently close, then the use of the initial boundary in the adjacent slices results in fast segmentation, without the need for editing.

Figure 12:
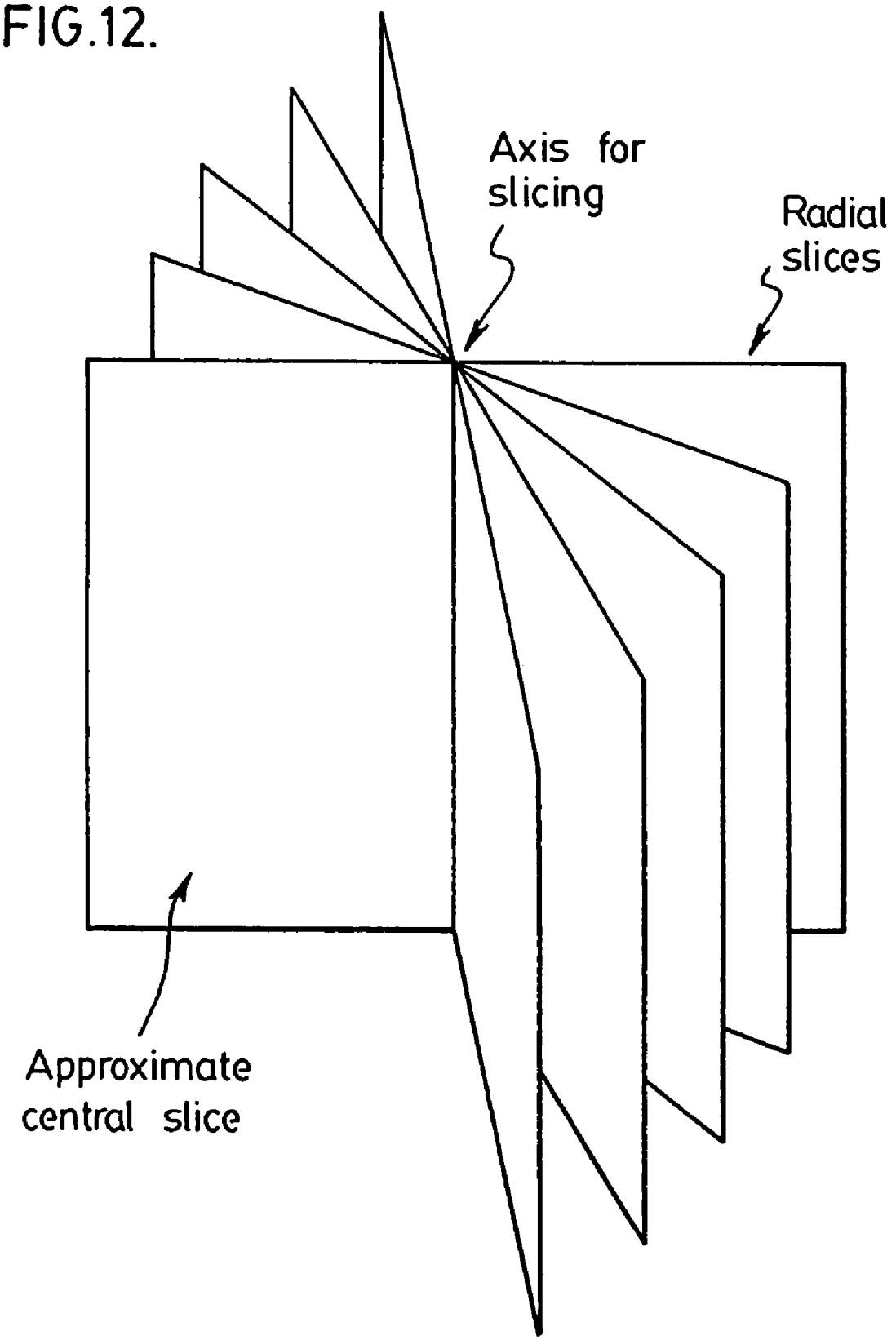
FIG. 12 shows a schematic diagram showing how the method to select sequences of 2D images out of the 3D volume to be used for the segmentation.

The 3D embodiment of the present invention has been successfully implemented using a 3D ultrasound image of a patient's prostate. The 3D image was sliced in parallel slices 1 mm apart to produce 35 transaxial slices of the prostate. The approximate central slice was chosen as the starting slice (i.e., slice number 15). The prostate in this slice was segmented by the technique described above using 4 seed points. This image required no editing, and the resulting boundary produced by the segmentation is shown in panel 15. This boundary was then used to initialize the segmentation of the adjacent slices 14 and 16. The resulting segmented boundary (without editing) is shown in panels 14 and 16 of FIG. 12. The segmented boundary in slice 14 was then used as the initial boundary for slice 13, and the segmented boundary in slice 16 was then used as the initial boundary for slice 17. This process continued until the segmentation of slices 1 and 34 was complete. The results of the complete process are shown in the panels of FIG. 12.

Figure 13:
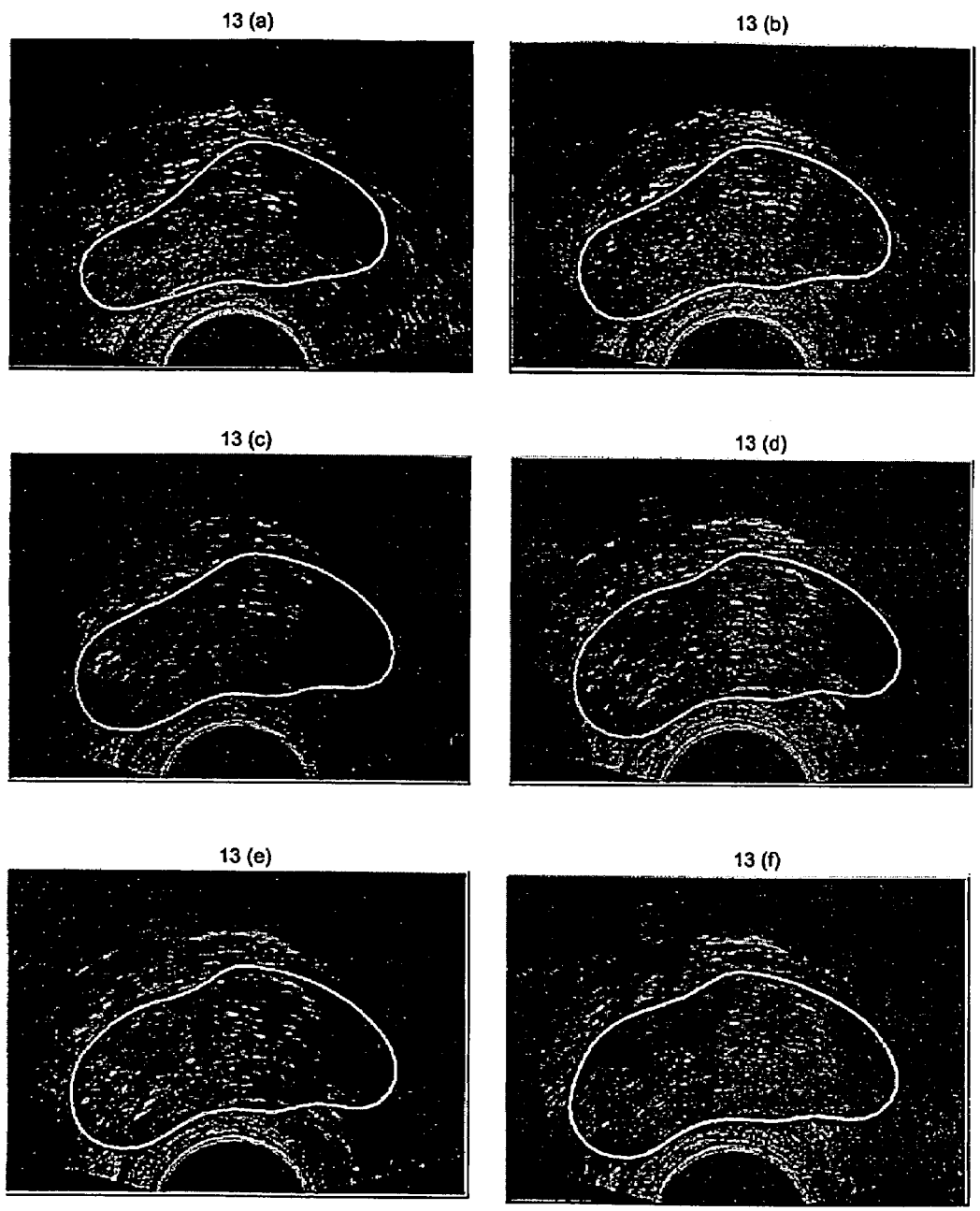
Figure 13:
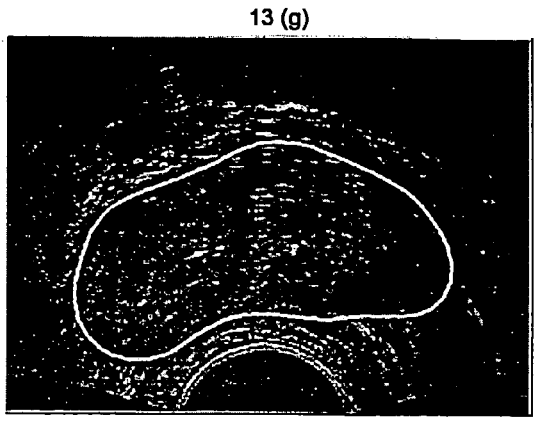
Figure 13:
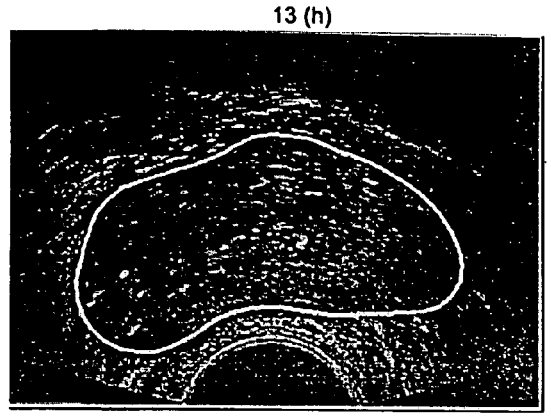
Figure 13:
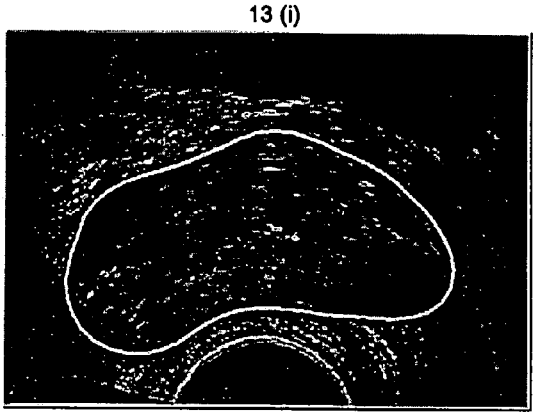
Figure 13:
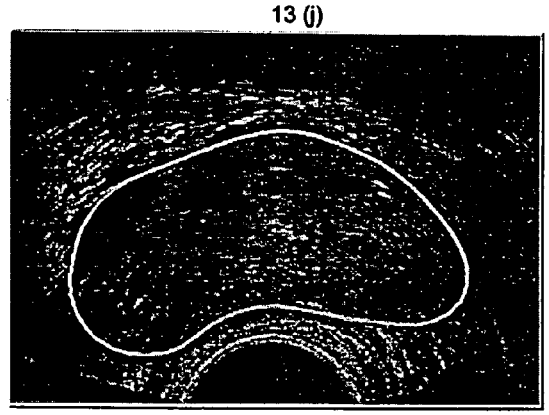
Figure 13:
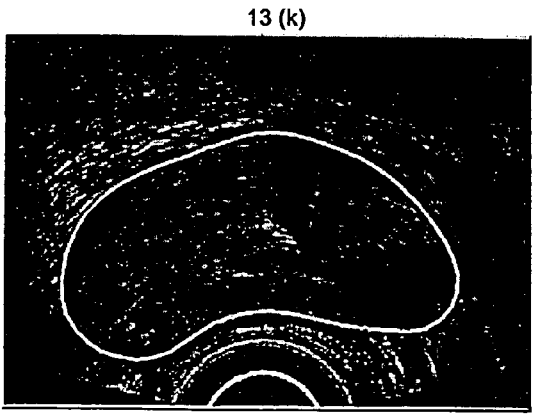
Figure 13:
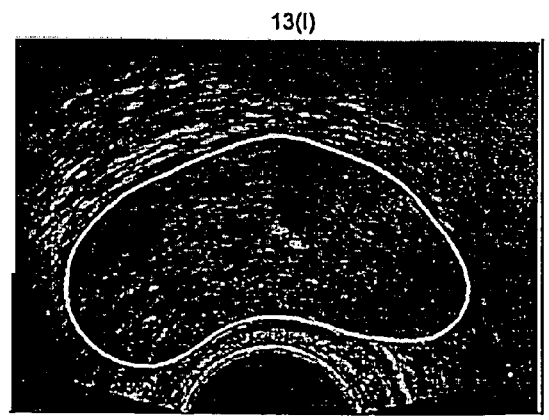
Figure 13:
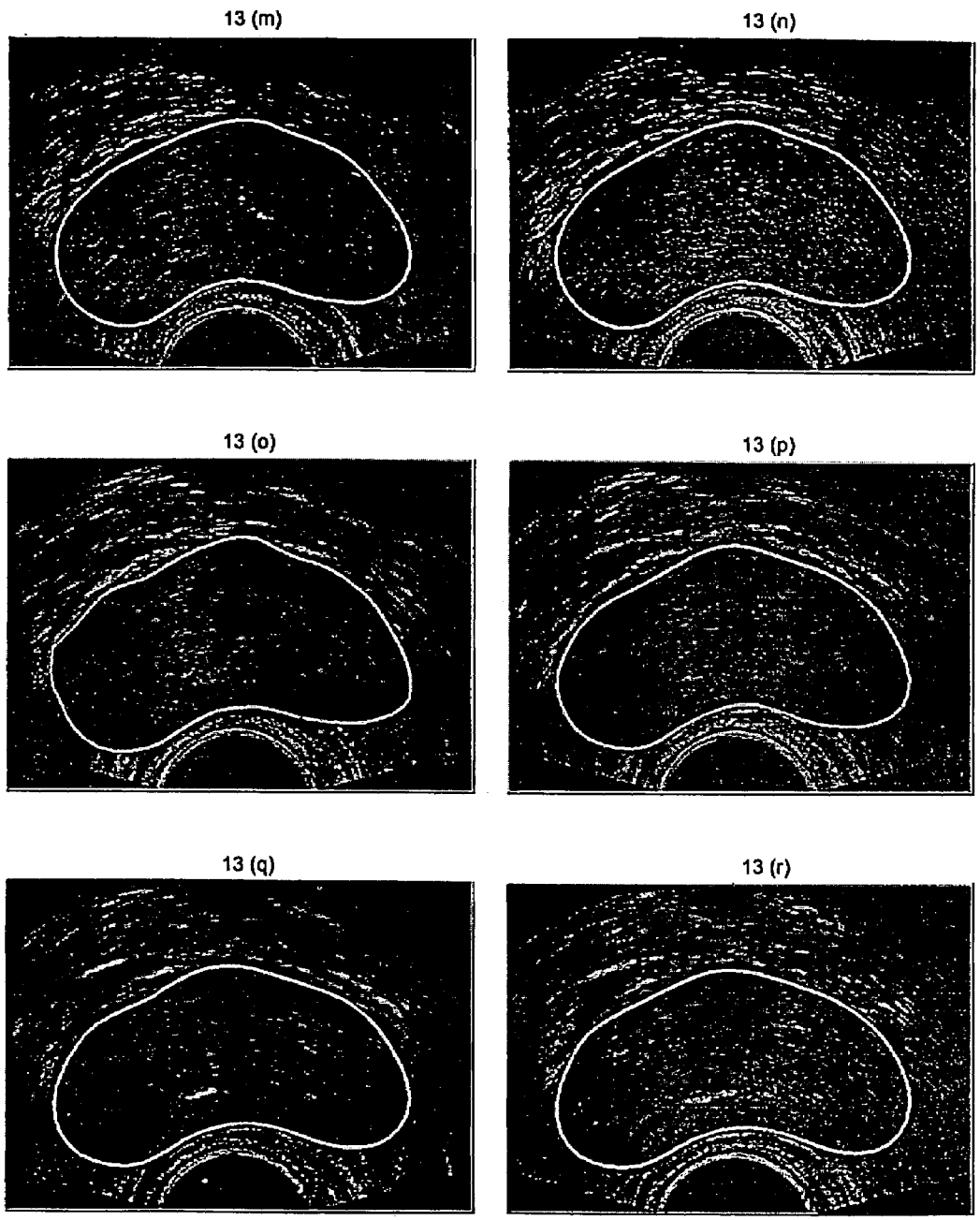
Figure 13:
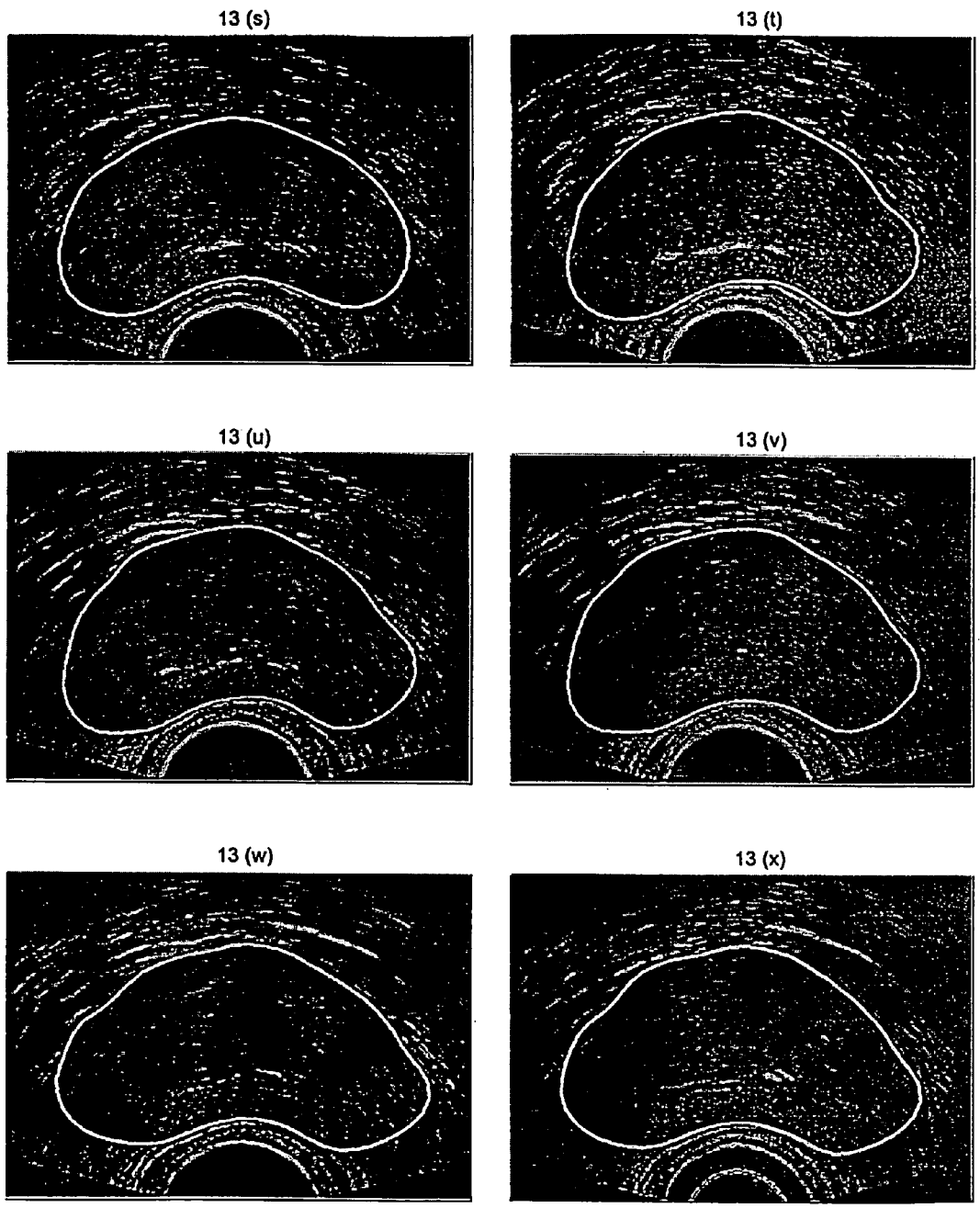
Figure 13:
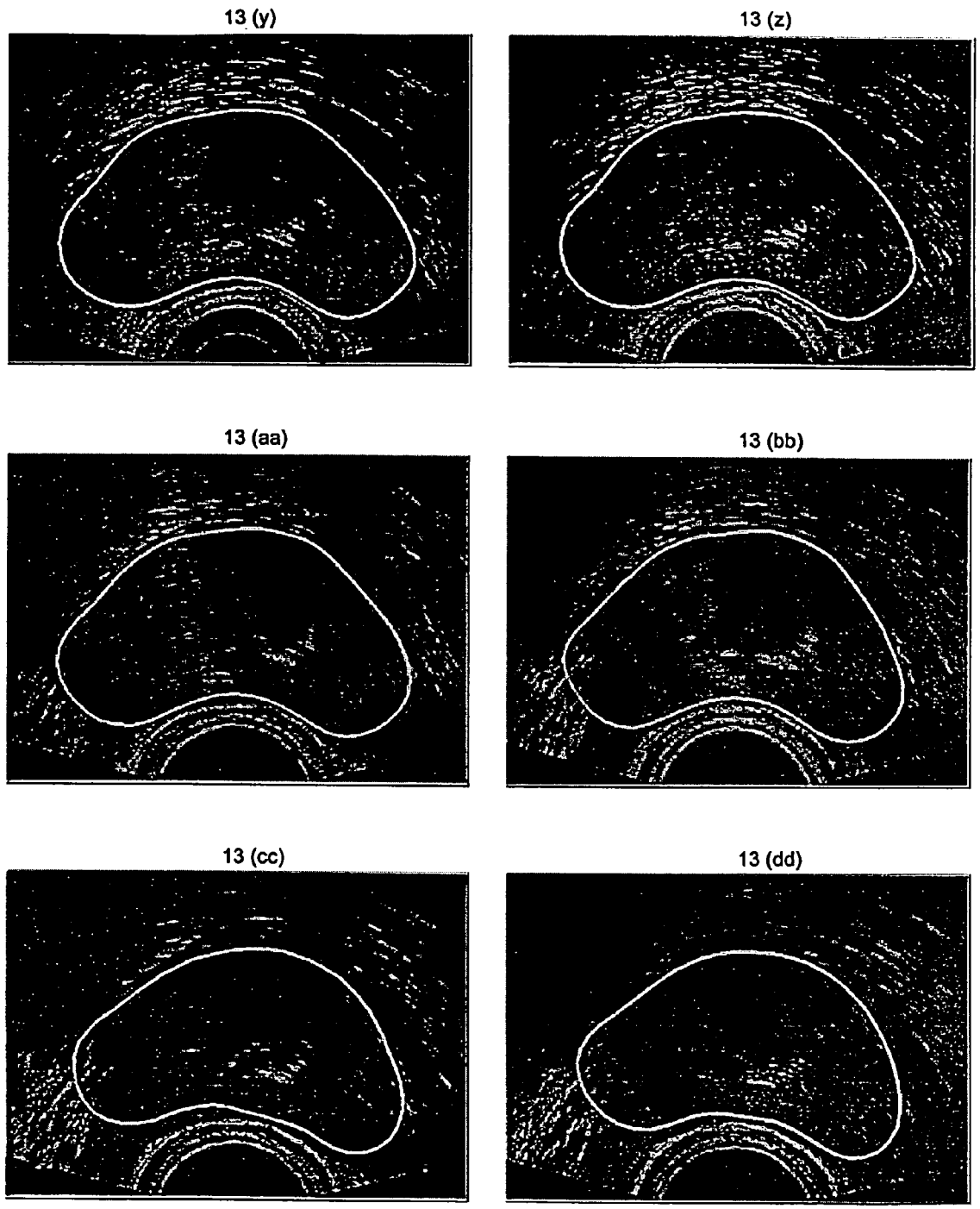
Figure 13:
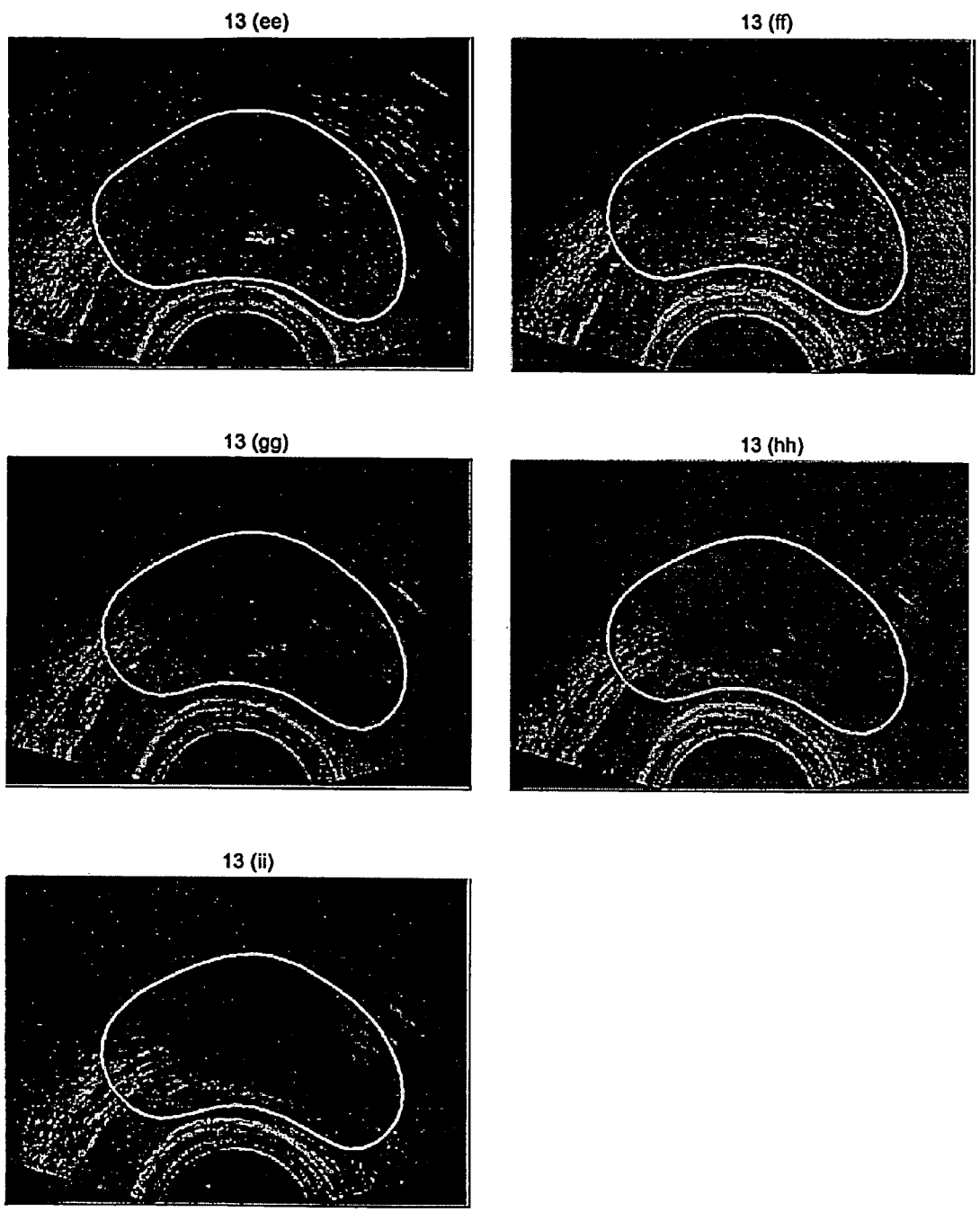

Although the example presented herein above was based on parallel transaxial slices, a person of ordinary skill in the art will appreciate that the prostate (or any 3D object) can be sliced in any regular manner for this 3D segmentation approach. For example, the prostate (or any 3D object) can be sliced in parallel slices in the coronal, sagittal or oblique direction, as well as in radial directions to produce radial slices with an axis through the center of the prostate (or any other axis) as shown in FIGS. 13(a) to 13(ii). The axis for radial slicing can be defined by the any two opposing points used as seed points to initialize the segmentation in the central slice. The radial slicing can be at equal angles, e.g., 1 degree, or varying angles depending on the complexity of the surface of the object.

All such embodiments and variations are believed to be within the sphere and scope of the invention as defined by the claims appended hereto.

What is claimed is:

1. A method of object segmentation using an image, comprising the steps of:

user selection of a first plurality of seed points in said image which lie at least approximately on a boundary of said object;

generating an initial contour of said object by interpolating additional seed points which lie at least approximately on said boundary using interpolation functions chosen to approximate the shape of said object; and automatically deforming at least said additional seed points based on boundary data from said image to generate a further plurality of points outlining the shape of said object.

2. The method of claim 1, further comprising the steps of interactively moving said further plurality of points and automatically deforming said further plurality of points to generate a final plurality of points outlining an edited shape of said object.

3. The method of claim 1, further comprising the step of clamping at least one of said first plurality of seed points or said further plurality of points at their respective positions prior to respective ones of said steps of automatically deforming.

4. The method of claim 1, wherein each said step of automatically deforming further comprises the step of converging each of said points on boundary edges of said object using a Discrete Dynamic Contour (DDC) algorithm.

5. The method of claim 1, wherein said step of electing said first plurality of seed points further comprises selecting first and third points lying approximately on a first axis of symmetry of said object and selecting second and fourth points lying approximately on a second axis of symmetry orthogonal to said first axis of symmetry.

6. The method of claim 5, wherein the step of generating said initial contour further comprises the step of (i) calculating respective coefficients of said interpolation functions from the respective positions of said first and third points, and said second and fourth points, and (ii) uniformly interpolating line segments between first and second points, said second and third points, said third and fourth points, and between said fourth and first points using said interpolation functions.

7. The method of claim 6, wherein the step of uniformly interpolating further comprises performing a Hermitian interpolatio of said line segments in accordance with first and second cubic interpolation functions.

8. The method of claim 4, wherein said step of converging each of said points on boundary edges of said object further comprises the step of modifying said Discrete Dynamic Contour (DDC) algorithm to apply image forces on said points only in the event that gray levels adjacent respective ones of said points vary from dark to light in an outward radial direction from each of said points.

9. The method of claim 4, wherein said step of converging each of said points on boundary edges of said object further comprises the step of maintaining respective distances between respective ones of each said points with successive iterations of said DDC algorithm at no less than 20 pixels.

10. The method of claim 1, further comprising the steps of selecting said further plurality of points outlining the shape of said object in one image plane through said object as respective ones of said additional seed points to which said step of automatically deforming is applied for an adjacent parallel image plane through said object in order to outline the shape of said object in three dimensions.

* * * * *